(12) United States Patent
Bonn et al.

(10) Patent No.: US 8,906,007 B2
(45) Date of Patent: Dec. 9, 2014

(54) ELECTROSURGICAL DEVICES, DIRECTIONAL REFLECTOR ASSEMBLIES COUPLEABLE THERETO, AND ELECTROSURGICAL SYSTEMS INCLUDING SAME

(75) Inventors: Kenlyn S. Bonn, Boulder, CO (US);
Darion Peterson, Boulder, CO (US);
Joseph D. Brannan, Erie, CO (US);
Kyle R. Rick, Boulder, CO (US)

(73) Assignee: Covidien LP, Mansfield, MA (US)

( * ) Notice: Subject to any disclaimer, the term of this patent is extended or adjusted under 35 U.S.C. 154(b) by 805 days.

(21) Appl. No.: 12/568,524

(22) Filed: Sep. 28, 2009

(65) Prior Publication Data
US 2011/0077633 A1    Mar. 31, 2011

(51) Int. Cl.
*A61B 18/18* (2006.01)
*A61B 18/00* (2006.01)
*A61B 19/00* (2006.01)

(52) U.S. Cl.
CPC ... *A61B 18/1815* (2013.01); *A61B 2018/00023* (2013.01); *A61B 2019/4054* (2013.01); *A61B 2019/4045* (2013.01); *A61B 2019/4081* (2013.01)
USPC .............................. 606/33; 606/41

(58) Field of Classification Search
USPC ....................................... 606/32–52
See application file for complete search history.

(56) References Cited

U.S. PATENT DOCUMENTS

| | | | |
|---|---|---|---|
| 3,539,034 A * | 11/1970 | Tafeen | 604/164.09 |
| 6,245,062 B1 | 6/2001 | Berube et al. | |
| 6,287,302 B1 | 9/2001 | Berube | |
| 6,312,427 B1 | 11/2001 | Berube et al. | |
| 6,364,876 B1 | 4/2002 | Erb et al. | |
| 6,383,182 B1 | 5/2002 | Berube et al. | |
| 6,527,768 B2 | 3/2003 | Berube | |
| 7,311,703 B2 | 12/2007 | Turovskiy et al. | |
| 7,326,201 B2 | 2/2008 | Fjield et al. | |
| 2001/0029368 A1 * | 10/2001 | Berube | 606/33 |
| 2002/0087151 A1 | 7/2002 | Mody et al. | |
| 2003/0060813 A1 | 3/2003 | Loeb et al. | |
| 2003/0060817 A1 * | 3/2003 | Sauvageau et al. | 606/32 |
| 2006/0027241 A1 * | 2/2006 | Malecki et al. | 128/898 |
| 2006/0116673 A1 | 6/2006 | Gauthier et al. | |
| 2006/0129213 A1 * | 6/2006 | Goldin | 607/101 |
| 2006/0241577 A1 * | 10/2006 | Balbierz et al. | 606/32 |
| 2006/0271032 A1 * | 11/2006 | Chin et al. | 606/41 |

(Continued)

FOREIGN PATENT DOCUMENTS

DE       390937        3/1924
DE      1099658        2/1961

(Continued)

OTHER PUBLICATIONS

U.S. Appl. No. 08/483,742, filed Jun. 7, 1995.

(Continued)

*Primary Examiner* — Michael Peffley
*Assistant Examiner* — Khadijeh Vahdat

(57) ABSTRACT

A directional reflector assembly includes a tubular shaft having a proximal end and a distal end and adapted to operably engage an electrosurgical ablation probe, and a conical aperture having a proximal open apex joined to a distal end of the tubular shaft, and a distal open base, wherein an interior volume of the tubular shaft is open to the conical aperture.

4 Claims, 14 Drawing Sheets

(56) References Cited

U.S. PATENT DOCUMENTS

| | | | |
|---|---|---|---|
| 2007/0265609 | A1 | 11/2007 | Thapliyal et al. |
| 2007/0265610 | A1 | 11/2007 | Thapliyal et al. |
| 2008/0269853 | A1* | 10/2008 | Kitanaka .................. 607/108 |
| 2008/0300590 | A1* | 12/2008 | Horne et al. ................ 606/35 |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 481 685 | 4/1992 |
| EP | 0 521 264 | 1/1993 |
| EP | 0 541 930 | 5/1993 |
| EP | 0 556 705 | 8/1993 |
| EP | 0 558 429 | 9/1993 |
| EP | 0 572 131 | 12/1993 |
| EP | 0 836 868 | 4/1998 |
| EP | 1 159 926 | 5/2001 |
| FR | 179607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| GB | 2 403 148 | 12/2004 |
| JP | 5843011 | 3/1983 |
| JP | H027602 A | 1/1990 |
| JP | 3103608 U | 10/1991 |
| JP | H03264882 A | 11/1991 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | 2004047659 A2 | 6/2004 |
| WO | WO 2008/012827 | 1/2008 |
| WO | 2008131306 A1 | 10/2008 |
| WO | 2009075904 A1 | 6/2009 |
| WO | WO2009075904 * | 6/2009 |
| WO | WO 2009/128940 | 10/2009 |

OTHER PUBLICATIONS

U.S. Appl. No. 08/136,098, filed Oct. 14, 1993.
U.S. Appl. No. 09/195,118, filed Nov. 18, 1998.
U.S. Appl. No. 10/244,346, filed Sep. 16, 2002.
U.S. Appl. No. 11/053,987, filed Feb. 8, 2005.
U.S. Appl. No. 12/023,606, filed Jan. 31, 2008.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/351,633, filed Jan. 9, 2009.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/401,268, filed Mar. 10, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.

(56) References Cited

OTHER PUBLICATIONS

Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnogtic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Cosman et al., "Methods of Making Nervous System Lesions" In William RH, Rengachary SS (eds): Neurosurgery, New York: McGraw•Hill, vol. 111, (1984), pp. 2490-2499.
Crawford et al., "Use of the LigaSure™ Vessel Sealing System in Urologic Cancer Surger" Grand Rounds In Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.

E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline Product Literature, "Light Key: Visualize a Virtual Keyboard. One With No Moving Parts", 4 pages.
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vase. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Johnson et al., "Evaluation of a Bipolar Electrothermal Vessel Sealing Device in Hemorrhoidectomy" Sales/Product Literature, Jan. 2004.
Jarrett et al., "Use of the LigaSure™ Vessel Sealing System for Peri-Hilar Vessels in Laparoscopic Nephrectomy" Sales/Product Literature 2000.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.

(56) References Cited

OTHER PUBLICATIONS

MDTech product literature (Mar. 2000) I'D Wire: product description, 1 page.
MDTech product literature (Dec. 1999) "FlexStrand": product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Oapril 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
S. Humphries Jr. et al., "Finite-Element Codes to Model Electrical Heating and Non•Llnear Thermal Transport in Biological Media", Proc. ASME HTD-355, 131 (1997).
Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Bums", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.

(56) References Cited

OTHER PUBLICATIONS

European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
Extended European Search Report for European Application No. EP10014705 dated Apr. 27, 2011 (5 Pages).
Extended European Search Report corresponding to EP 10 01 0942.0, completed Sep. 7, 2011 and mailed Sep. 16, 2011; (8 pp).
Translation of Japanese Office Action mailed Feb. 18, 2014, in counterpart JP Application No. 2010-214756; (2 pp).

\* cited by examiner

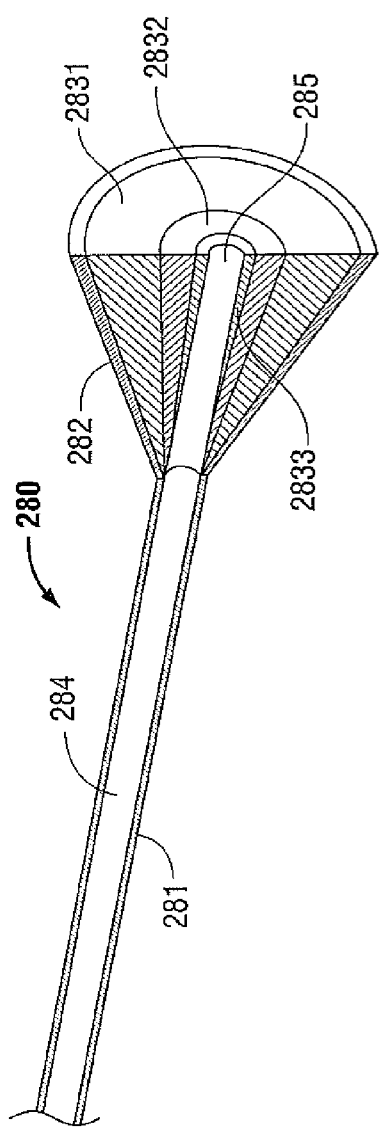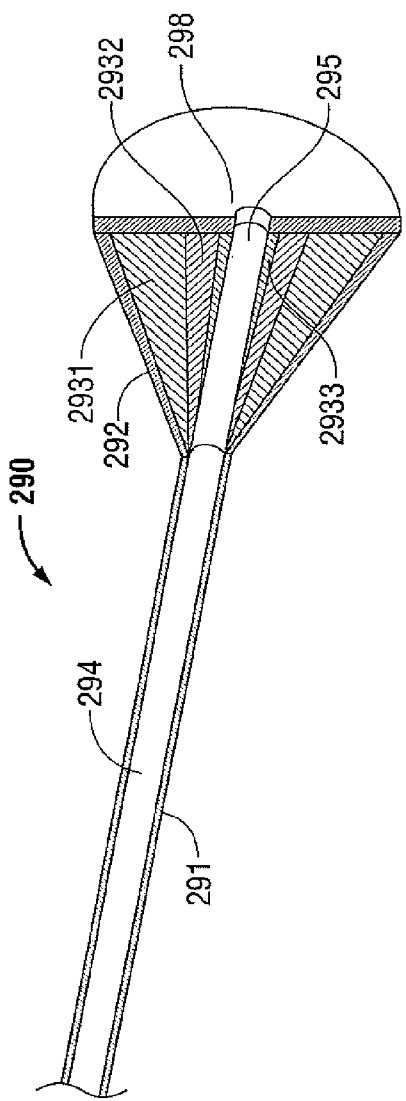
FIG. 19
FIG. 20

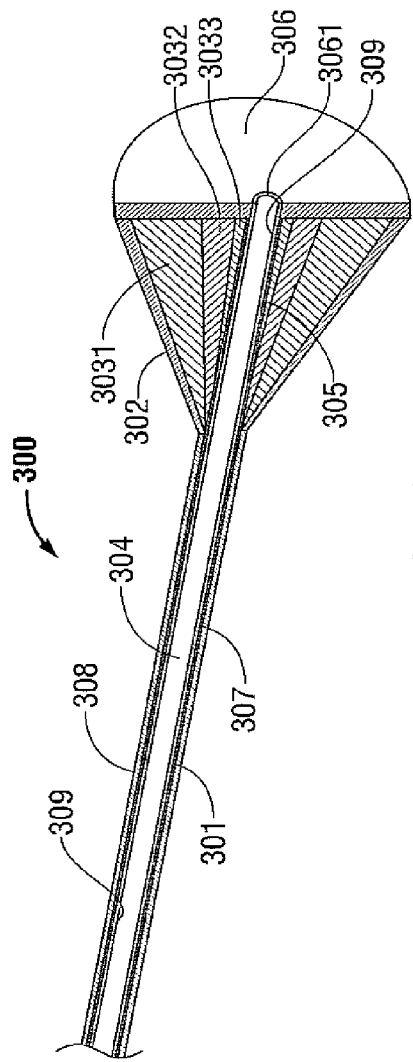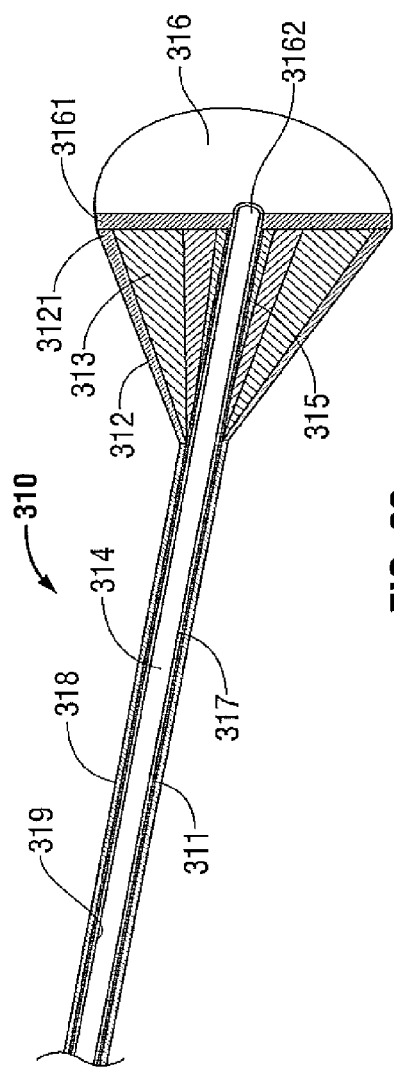

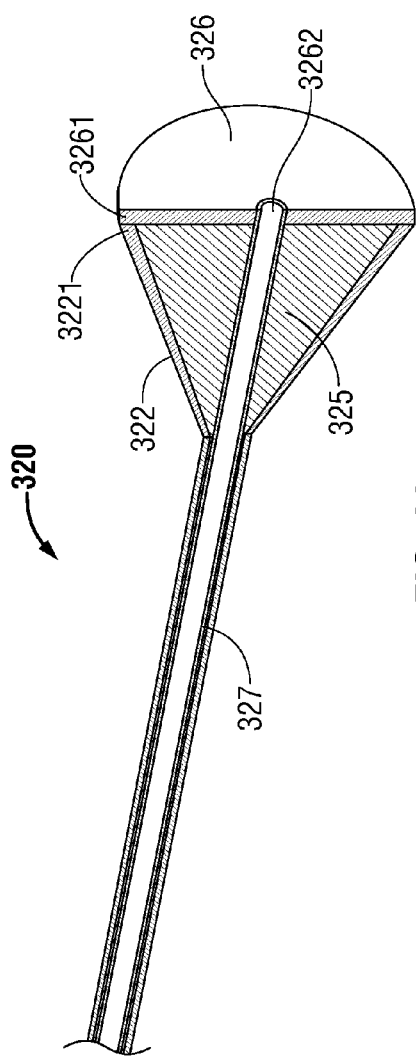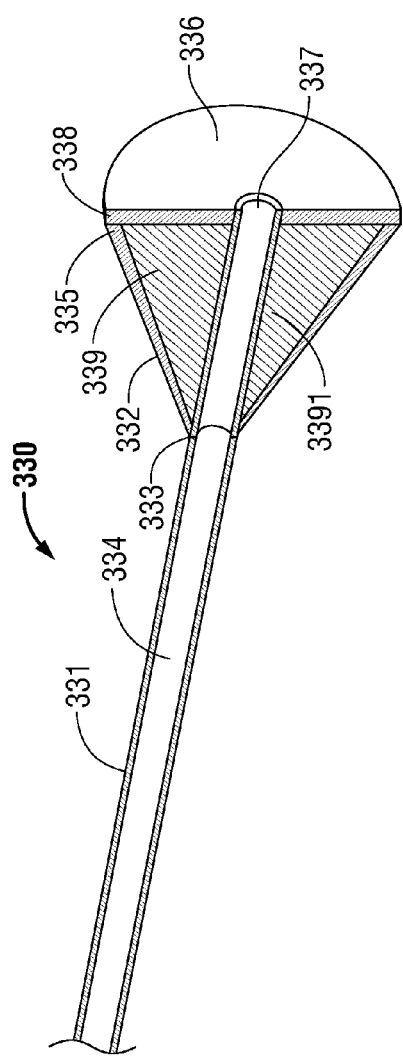

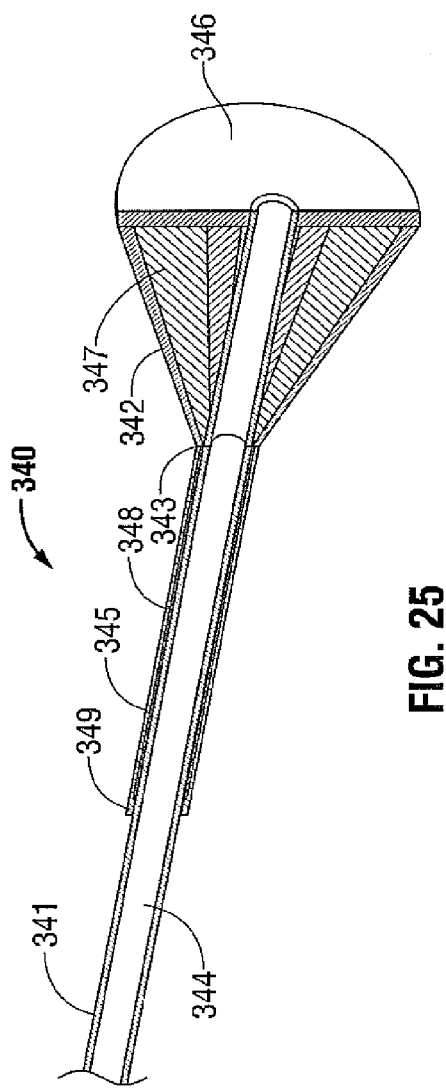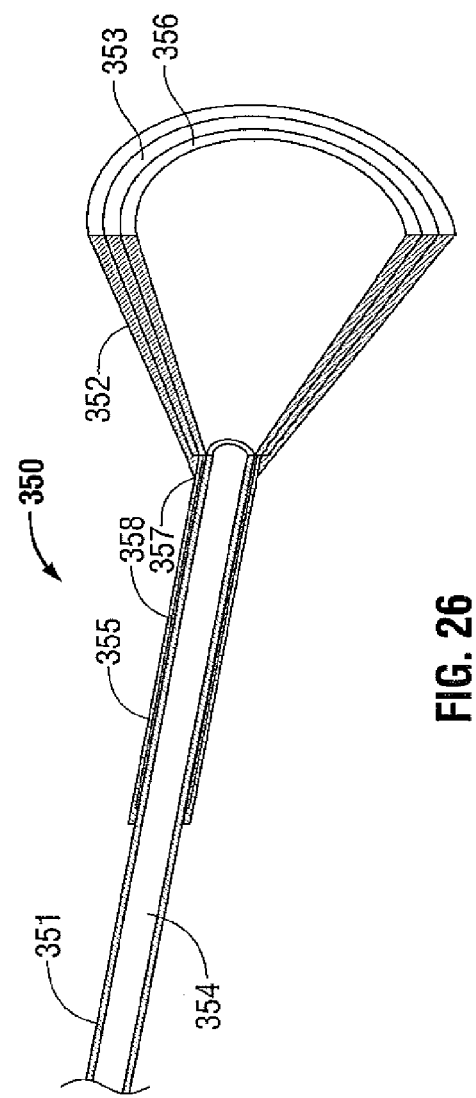
FIG. 25
FIG. 26

ELECTROSURGICAL DEVICES, DIRECTIONAL REFLECTOR ASSEMBLIES COUPLEABLE THERETO, AND ELECTROSURGICAL SYSTEMS INCLUDING SAME

BACKGROUND

1. Technical Field

The present disclosure relates to electrosurgical devices suitable for use in tissue ablation applications and, more particularly, to electrosurgical devices, directional reflector assemblies coupleable thereto, and electrosurgical systems including the same.

2. Discussion of Related Art

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic radiation to heat, ablate and/or coagulate tissue. Microwave energy is sometimes utilized to perform these methods. Other procedures utilizing electromagnetic radiation to heat tissue also include coagulation, cutting and/or ablation of tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator that functions as an energy source, and a microwave surgical instrument (e.g., microwave ablation probe) having an antenna assembly for directing the energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

There are several types of microwave probes in use, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors that are linearly aligned and positioned end-to-end relative to one another with an electrical insulator placed therebetween. Helical antenna assemblies include helically-shaped conductor configurations of various diameters and dimensions. The main modes of operation of a helical antenna assembly are normal mode (broadside), in which the field radiated by the helix is maximum in a perpendicular plane to the helix axis, and axial mode (end fire), in which maximum radiation is along the helix axis.

A microwave transmission line typically includes a long, thin inner conductor that extends along the longitudinal axis of the transmission line and is surrounded by a dielectric material and is further surrounded by an outer conductor around the dielectric material such that the outer conductor also extends along the transmission line axis. In one variation of an antenna, a waveguiding structure, such as a length of transmission line or coaxial cable, is provided with a plurality of openings through which energy "leaks" or radiates away from the guiding structure. This type of construction is typically referred to as a "leaky coaxial" or "leaky wave" antenna.

Cooling the ablation probe may enhance the overall heating pattern of the antenna, prevent damage to the antenna and prevent harm to the clinician or patient. Because of the small temperature difference between the temperature required for denaturing malignant cells and the temperature normally injurious to healthy cells, a known heating pattern and precise temperature control is needed to lead to more predictable temperature distribution to eradicate the tumor cells while minimizing the damage to surrounding normal tissue.

During certain procedures, it can be difficult to assess the extent to which the microwave energy will radiate into the surrounding tissue, making it difficult to determine the area or volume of surrounding tissue that will be ablated. In some instances, targeted lesions may be located on or near the surface of the target organ. Such surface lesions have been treated with invasive ablation needles or sticks, which may cause damage to adjacent anatomical structures, increase the likelihood of hemorrhaging, and lengthen operative and recovery times.

SUMMARY

The present disclosure relates to a directional reflector assembly including a tubular shaft having a proximal end and a distal end and adapted to operably engage an electrosurgical ablation probe, and a conical aperture having a proximal open apex joined to a distal end of the tubular shaft, and a distal open base, wherein an interior volume of the tubular shaft is open to the conical aperture.

The present disclosure also relates to a directional reflector assembly including a tubular inner shaft having a proximal end and a distal end and adapted to operably engage an electrosurgical ablation probe, a tubular outer shaft coaxially-disposed about the inner shaft to define a fluid conduit therebetween, and a conical aperture having a proximal open apex joined to a distal end of the tubular outer shaft, and a distal open base, wherein an interior volume of the tubular inner shaft is in fluid communication with the conical aperture.

The present disclosure also relates to an electrosurgical ablation system including a source of microwave ablation energy, a microwave ablation probe operably coupled to the source of microwave ablation energy, wherein the microwave ablation probe includes a proximal handle portion and a distal shaft portion, and at least one protrusion disposed at a proximal end of the shaft that is adapted to operably engage a slot provided by a directional reflector assembly.

The present disclosure also relates to a method of operating an electrosurgical ablation system including the steps of providing a source of microwave ablation energy and providing a microwave ablation probe adapted to operably coupled to the source of microwave ablation energy, wherein the microwave ablation probe includes a proximal handle portion and a distal shaft portion. The method also includes the steps of operably coupling a directional reflector assembly to the probe and activating the source of microwave energy.

BRIEF DESCRIPTION OF THE DRAWINGS

Objects and features of the presently disclosed electrosurgical devices and directional reflector assemblies coupleable thereto will become apparent to those of ordinary skill in the art when descriptions of various embodiments thereof are read with reference to the accompanying drawings, of which:

FIG. 19 is a perspective view of an embodiment of a directional reflector assembly in accordance with the present disclosure that includes a conical aperture having a plurality of dielectric layers;

FIG. 20 is a perspective view of an embodiment of a directional reflector assembly in accordance with the present disclosure that includes a conical aperture having a plurality of dielectric layers and an end cap;

FIG. 21 is a perspective view of an embodiment of a directional reflector assembly in accordance with the present disclosure that includes a cooled shaft and a conical aperture having a plurality of dielectric layers;

FIG. 22 is a perspective view of an embodiment of a directional reflector assembly in accordance with the present disclosure that includes a cooled shaft and a conical aperture having fluid- and dielectric-filled regions;

FIG. 23 is a perspective view of an embodiment of a directional reflector assembly in accordance with the present disclosure that includes a cooled shaft and a coolant-filled conical aperture and an end cap;

FIG. 24 is a perspective view of an embodiment of a directional reflector assembly in accordance with the present disclosure that includes a conical aperture having fluid- and dielectric-filled regions;

FIG. 25 is a perspective view of an embodiment of a directional reflector assembly in accordance with the present disclosure that includes a dielectric-filled conical aperture and a balun positioned over the shaft;

FIG. 26 is a perspective view of an embodiment of a directional reflector assembly in accordance with the present disclosure that includes an air-filled conical aperture and a balun positioned over the shaft and within the cone.

DETAILED DESCRIPTION

Figure 1:
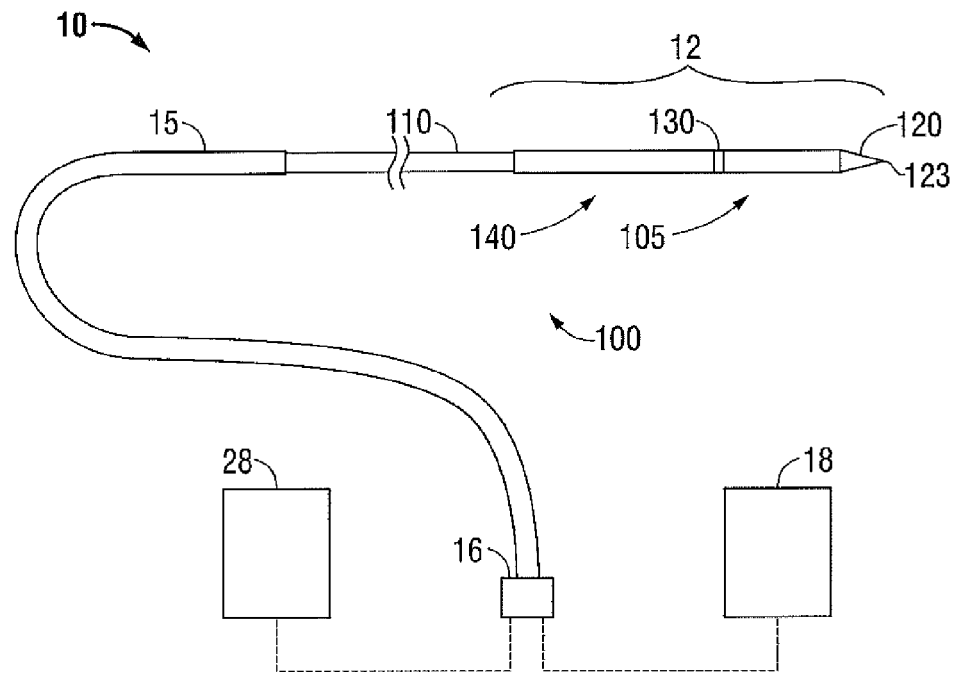
FIG. 1 is a schematic diagram of an ablation system in accordance with an embodiment of the present disclosure.

Hereinafter, embodiments of the presently disclosed electrosurgical devices, directional reflector assemblies coupleable thereto, and electrosurgical system including the same will be described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus that is closer to the user and the term "distal" refers to that portion of the apparatus that is farther from the user.

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As it is used in this description, "ablation procedure" generally refers to any ablation procedure, such as microwave ablation, radio frequency (RF) ablation or microwave ablation assisted resection. As it is used in this description, "transmission line" generally refers to any transmission medium that can be used for the propagation of signals from one point to another.

Various embodiments of the present disclosure provide electrosurgical devices operably associated with directional reflector assemblies for treating tissue and methods of directing electromagnetic radiation to a target volume of tissue. Embodiments may be implemented using electromagnetic radiation at microwave frequencies or at other frequencies. An electrosurgical system including an energy applicator operably associated with a directional reflector assembly, according to various embodiments, is designed and configured to operate between about 500 MHz and about 10 GHz with a directional radiation pattern.

Various embodiments of the presently disclosed electrosurgical devices, directional reflector assemblies coupleable thereto and electrosurgical system including the same are suitable for microwave ablation and for use to pre-coagulate tissue for microwave ablation assisted surgical resection. Although various methods described hereinbelow are targeted toward microwave ablation and the complete destruction of target tissue, it is to be understood that methods for directing electromagnetic radiation may be used with other therapies in which the target tissue is partially destroyed or damaged, such as, for example, to prevent the conduction of electrical impulses within heart tissue. In addition, although the following description describes the use of a dipole microwave antenna, the teachings of the present disclosure may also apply to a monopole, helical, or other suitable type of microwave antenna.

FIG. 1 shows an electrosurgical system 10, according to an embodiment of the present disclosure that includes an energy applicator or probe 100. Probe 100 generally includes an antenna assembly 12 having a radiating portion connected by a feedline 110 (or shaft) via a transmission line 15 to a connector 16, which may further operably connect the probe 100 to an electrosurgical power generating source 28, e.g., a microwave or RF electrosurgical generator.

Feedline 110 may be formed from any suitable flexible, semi-rigid or rigid microwave conductive cable and may connect directly to an electrosurgical power generating source 28. Alternatively, the feedline 110 may electrically connect the antenna assembly 12 via the transmission line 15 to the electrosurgical power generating source 28. Feedline 110 may have a variable length from a proximal end of the antenna assembly 12 to a distal end of transmission line 15 ranging from a length of about one inch to about twelve inches. Feedline 110 may be formed of suitable electrically conductive materials, e.g., copper, gold, silver or other conductive metals having similar conductivity values. Feedline 110 may be made of stainless steel, which generally offers the strength required to puncture tissue and/or skin. Conductive materials used to form the feedline 110 may be plated with other materials, e.g., other conductive materials, such as gold or silver, to improve their properties, e.g., to improve conductivity, decrease energy loss, etc. In some embodiments, the feedline 110 includes stainless steel, and to improve the conductivity thereof, the stainless steel may be coated with a layer of a conductive material such as copper or gold. Feedline 110 may include an inner conductor, a dielectric material coaxially surrounding the inner conductor, and an outer conductor coaxially surrounding the dielectric material. Antenna assembly 12 may be formed from a portion of the inner conductor that extends distal of the feedline 110 into the antenna assembly 12. Feedline 110 may be cooled by fluid e.g., saline or water, to improve power handling, and may include a stainless steel catheter.

In some embodiments, the power generating source 28 is configured to provide microwave energy at an operational frequency from about 500 MHz to about 2500 MHz. In other embodiments, the power generating source 28 is configured to provide microwave energy at an operational frequency from about 500 MHz to about 10 GHz. Power generating source 28 may be configured to provide various frequencies of electromagnetic energy. Transmission line 15 may additionally, or alternatively, provide a conduit (not shown) configured to provide coolant from a coolant source 18 to the probe 100.

Located at the distal end of the antenna assembly 12 is an end cap or tapered portion 120 that may terminate in a sharp tip 123 to allow for insertion into tissue with minimal resistance. The end cap or tapered portion 120 may include other shapes, such as, for example, a tip 123 that is rounded, flat, square, hexagonal, or cylindroconical.

In some variations, the antenna assembly 12 includes a distal radiating portion 105 and a proximal radiating portion 140. A junction member 130 may be provided. Junction member 130, or portions thereof, may be disposed between the proximal and distal radiating portions, 140 and 105, respectively. In some embodiments, the distal and proximal radiating portions 105, 140 align at the junction member 130, which is generally made of a dielectric material, e.g., adhesives, and are also supported by the inner conductor that extends at least partially through the distal radiating portion 105. Junction member 130 may be formed from any suitable elastomeric or ceramic dielectric material by any suitable process. In some embodiments, the junction member 130 is formed by overmolding and includes a thermoplastic elastomer, such as, for example, polyether block amide (e.g., PEBAX®, manufactured by The Arkema Group of Colombes, France), polyetherimide (e.g., ULTEM® and/or EXTEM®, manufactured by SABIC Innovative Plastics of Saudi Arabia) and/or polyimide-based polymer (e.g., VESPEL®, manufactured by E. I. du Pont de Nemours and Company of Wilmington, Del., United States). Junction member 130 may be formed using any suitable over-molding compound by any suitable process, and may include use of a ceramic substrate.

In some embodiments, the antenna assembly 12 may be provided with a coolant chamber (not shown). Additionally, the junction member 130 may include coolant inflow and outflow ports (not shown) to facilitate the flow of coolant into, and out of, the coolant chamber. Examples of coolant chamber and coolant inflow and outflow port embodiments are disclosed in commonly assigned U.S. patent application Ser. No. 12/401,268 filed on Mar. 10, 2009, entitled "COOLED DIELECTRICALLY BUFFERED MICROWAVE DIPOLE ANTENNA", and U.S. Pat. No. 7,311,703, entitled "DEVICES AND METHODS FOR COOLING MICROWAVE ANTENNAS".

In some embodiments, the antenna assembly 12 may be provided with an outer jacket (not shown) disposed about the distal radiating portion 105, the junction 130 and/or the proximal radiating portion 140. The outer jacket may be formed of any suitable material, such as, for example, polymeric or ceramic materials. The outer jacket may be applied by any suitable method, such as, for example, heat shrinking, overmolding, coating, spraying dipping, powder coating, baking and/or film deposition. The outer jacket may be a water-cooled catheter formed of a material having low electrical conductivity.

During microwave ablation, e.g., using the electrosurgical system 10, the probe 100 is inserted into or placed adjacent to tissue and microwave energy is supplied thereto. Ultrasound or computed tomography (CT) guidance may be used to accurately guide the probe 100 into the area of tissue to be treated. Probe 100 may be placed percutaneously or surgically, e.g., using conventional surgical techniques by surgical staff. A clinician may pre-determine the length of time that microwave energy is to be applied. Application duration may depend on many factors such as tumor size and location and whether the tumor was a secondary or primary cancer. The duration of microwave energy application using the probe 100 may depend on the progress of the heat distribution within the tissue area that is to be destroyed and/or the surrounding tissue. Single or multiple probes 100 may provide ablations in short procedure times, e.g., a few minutes, to destroy cancerous cells in the target tissue region.

A plurality of probes 100 may be placed in variously-arranged configurations to substantially simultaneously ablate a target tissue region, making faster procedures possible. Multiple probes 100 can be used to synergistically create a large ablation or to ablate separate sites simultaneously. Tissue ablation size and geometry is influenced by a variety of factors, such as the energy applicator design, number of energy applicators used simultaneously, time and wattage.

In operation, microwave energy having a wavelength, lamda ($\lambda$), is transmitted through the antenna assembly 12, e.g., along the proximal and distal radiating portions 140, 105, and radiated into the surrounding medium, e.g., tissue. The length of the antenna for efficient radiation may be dependent on the effective wavelength $\lambda_{\it eff}$ that is dependent upon the dielectric properties of the medium being radiated. Antenna assembly 12 through which microwave energy is transmitted at a wavelength $\lambda$ may have differing effective wavelengths $\lambda_{\it eff}$ depending upon the surrounding medium, e.g., liver tissue, as opposed to breast tissue.

Figure 2:
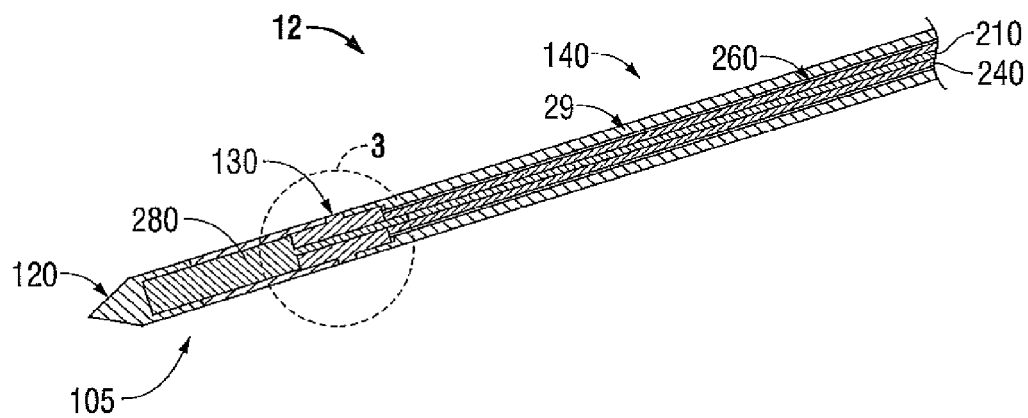
FIG. 2 is a partial, longitudinal cross-sectional view of an embodiment of the energy applicator of the ablation system shown in FIG. 1 in accordance with the present disclosure.
Figure 3:
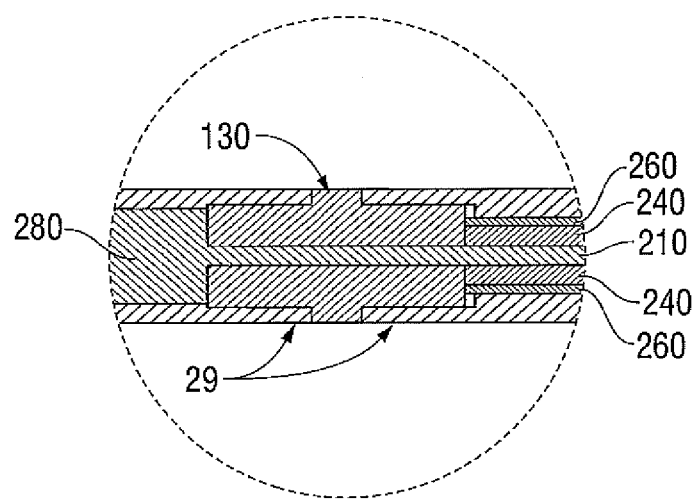
FIG. 3 is an enlarged view of the indicated area of detail of FIG. 2 according to an embodiment of the present disclosure.

Referring to FIGS. 2 and 3, an embodiment of the antenna assembly 12 of FIG. 1 is shown and includes an inner conductor 210, an outer conductor 260, and may include a first dielectric material 240 separating the inner conductor 210 and the outer conductor 260. In some embodiments, the inner conductor 210 is formed from a first electrically conductive material (e.g., stainless steel) and the outer conductor 260 is formed from a second electrically conductive material (e.g., copper). In some embodiments, the outer conductor 260 coaxially surrounds the inner conductor 210 along a distal portion of the antenna assembly 12, e.g., as shown in FIG. 2. Inner conductor 210 and the outer conductor 260 may be formed from any suitable electrically conductive material.

First dielectric material 240 may be formed from any suitable dielectric material. including, but not limited to, ceramics, water, mica, polyethylene, polyethylene terephthalate, polyimide, polytetrafluoroethylene (a.k.a. PTFE or Teflon®, manufactured by E. I. du Pont de Nemours and Company of Wilmington, Del., United States), glass, or metal oxides. Antenna assembly 12 may be provided with a second dielectric material 29 surrounding the outer conductor 260 and/or the puck 130, or portions thereof. Second dielectric material 29 may be formed from any suitable dielectric material. In some embodiments, the second dielectric material 29 is formed from a material with a dielectric constant different than the dielectric constant of the first dielectric material 240.

In some embodiments, the antenna assembly 12 includes a conductor end portion 280, which may be formed from any suitable electrically conductive material. In some embodiments, the conductor end portion 280 is coupled to the inner conductor 210 and may be formed of the same material as the inner conductor 210. As shown in FIG. 2, the conductor end portion 280 may be spaced apart from the outer conductor 260 by the puck 130 disposed therebetween. Tapered region 120, or portions thereof, may surround a proximal portion of the conductor end portion 280. In some embodiments, the conductor end portion 280 is substantially cylindrically shaped, and may be formed from stainless steel. The shape and size of the conductor end portion 280 may be varied from the configuration depicted in FIG. 2. In some embodiments, at least a portion of the conductor end portion 280 is surrounded by the second dielectric material 29.

Figure 4:
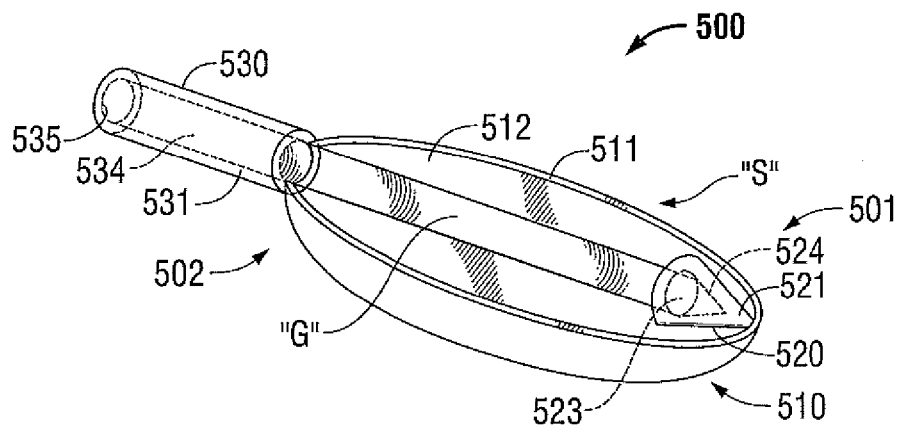
FIG. 4 is a perspective view of an embodiment of a directional reflector assembly in accordance with the present disclosure.

FIG. 4 shows a directional reflector assembly 500 according to an embodiment of the present disclosure that includes a shell assembly 510, a first attachment portion 520 disposed at the distal end portion 501 of the shell assembly 510, and a second attachment portion 530 that extends proximally from the proximal end 502 of the shell assembly 510. First attachment portion 520 may have a substantially conical shape, and may be formed of any suitable material, such as metal. Second attachment portion 530 may have a substantially cylindrical shape, and may be formed of any suitable material, such as a generally flexible and resilient thermoplastic material and/or metal. In embodiments, the second attachment portion 530 may be replaceable (e.g., removeably coupleable to the shell assembly 510, such as by a threaded fastener), thereby providing the capability to use second attachment portions 530 of different diameters to accommodate varied ablation probe diameters.

Shell assembly 510 may be shaped in such a manner to provide a desired surface ablation shape as well as aid in impedance matching. For example, the shell assembly 510 may taper from a diameter similar to the diameter of the second attachment portion 530 to a larger diameter as the shell assembly 510 extends proximally. Shell assembly 510 may have any suitable shape and may be designed for tight spaces encountered during surgical operations. For example, the shell assembly 510 may have a shape similar to the shape of a thick butter knife (e.g., 921 shown in FIG. 14A) or a half-conical shape (e.g., 931 shown in FIG. 14B).

Figure 5:
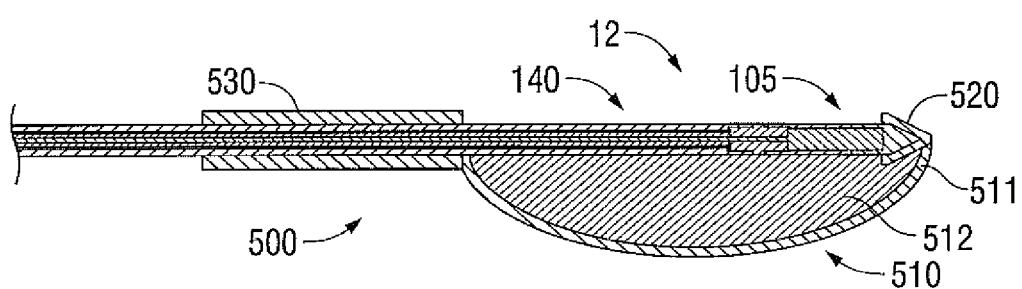
FIG. 5 is a partial, cross-sectional view of the energy applicator of FIG. 2 shown operably associated with the directional reflector assembly of FIG. 4.

As shown in FIGS. 4 and 5, the shell assembly 510 generally includes an outer portion 511 and an inner portion 512, and may include a recess in the form of a groove "G" defined in the planar surface "S" of the inner portion 512 generally configured to receive a portion of an energy applicator therein. As shown in FIG. 5, a portion of the antenna assembly 12 (e.g., distal radiating portion 105 and proximal radiating portion 140) may be disposed within the groove "G" in the inner portion 512.

Outer portion 511 may include an electrically conductive material, such as, for example, copper, stainless steel, titanium, titanium alloys such as nickel-titanium and titanium-aluminum-vanadium alloys, aluminum, aluminum alloys, tungsten carbide alloys or combinations thereof. Portions of the outer portion 511 may be loaded with low- to mid-range permittivity dielectric materials to aid in radiation directivity and impedance matching. In general, the dielectric permittivity would increase in value with radial distance from the electrically-conductive member 511. Several shells, or other shapes, of different dielectric materials may nest together to form the outer portion 511.

Inner portion 512 may include a dielectric material. In some embodiments, the inner portion 512 includes dielectric material layers. For example, the inner portion 512 may include one or more thin layers, one or more thick layers or a mixture of thick and thin layers. Inner portion 512 may be composed of any suitable dielectric material which may be the same as, or different from, the dielectric material, if any, used in the outer portion 511. The dielectric materials used to form the inner portion 512 may vary in dielectric constant with shells (e.g., 7171, 7172 and 7173 shown in FIG. 10) or more complex dielectric layering to achieve the optimum antenna directivity and energy to tissue delivery. In embodiments, the dielectric material used to form the inner portion 512 may have a relatively high dielectric constant k (e.g., k≈80) to enhance the directional influence of the electromagnetic field.

First and second attachment portions, 520 and 530, may be formed of any suitable material, such as metal. In embodiments, the second attachment portion 530 includes a tubular body 531 defining a lumen 534 into which a proximal portion of the antenna assembly 12 may be positioned. Tubular body 531 may be provided with an inner liner (not shown) disposed in contact with the inner surface 535, or portion thereof, of the lumen 534, wherein the inner liner is configured to frictionally engage at least a portion of the outer surface of an energy applicator shaft disposed within the lumen 534 when the directional reflector assembly 500 is operably associated with the energy applicator. An outer sleeve (not shown) may additionally, or alternatively, be provided to at least a portion of an energy applicator, wherein the outer sleeve is adapted to frictionally engage the inner surface 535 of the lumen 534. In embodiments, the second attachment portion 530, or portion thereof, is formed of a generally flexible and/or resilient material, e.g., silicon rubber, and may be provided with a fastener element (e.g., 660 shown in FIG. 7B) disposed around the outer surface thereof, e.g., for releaseably securing a proximal portion of an energy applicator disposed within the lumen 534.

First attachment portion 520 generally includes a body 521 defining a chamber 524 therein and an opening in communication with the groove "G". Opening 523 and the chamber 524 are generally configured to receive the distal end portion of an energy applicator, e.g., tip 123 of the antenna assembly 12. The shape and size of the first and second attachment portions, 520 and 530, may be varied from the configuration depicted in FIG. 4.

Figure 6:
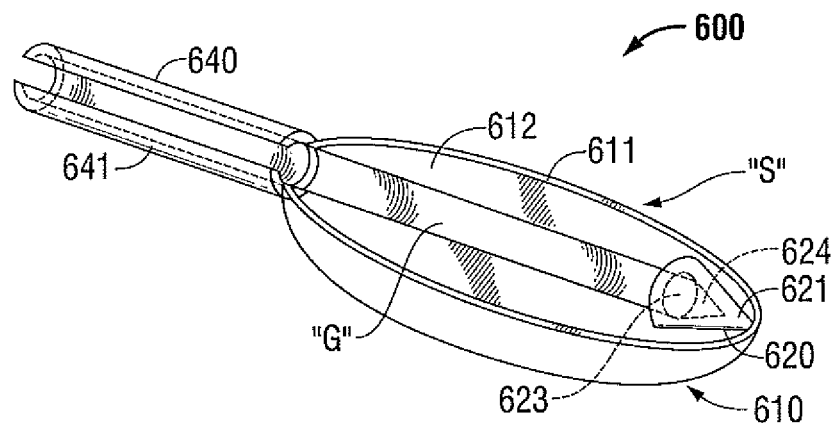
FIG. 6 is a perspective view of another embodiment of a directional reflector assembly in accordance with the present disclosure.

FIG. 6 shows a directional reflector assembly 600 according to an embodiment of the present disclosure that includes a shell assembly 610, a first attachment portion 620, and a second attachment portion 640. Shell assembly 610 generally includes an outer portion 611 and an inner portion 612, and may include a recess in the form of a groove "G" defined in the planar surface "S" of the inner portion 612 generally configured to receive a portion of an energy applicator therein. Shell assembly 610 is similar to the shell assembly 510 shown in FIG. 4, and further description thereof is omitted in the interests of brevity.

First attachment portion 620 generally includes a body 621 defining a chamber 624 therein and an opening in communication with the groove "G" defined in the inner portion 612. First attachment portion 620 is similar to the first attachment portion 520 shown in FIG. 4, and further description thereof is omitted in the interests of brevity.

Second attachment portion 640 extends proximally from the proximal end of the shell assembly 610. Second attachment portion 640 is similar to the second attachment portion 530 shown in FIG. 4, except for its shape. In embodiments the second attachment portion 640 includes a body 641 having a partial, cylindrical shape (e.g., a partial cylinder with a substantially C-shaped cross section) of any suitable length. Second attachment portion 640 may be formed of any suitable rigid, semi-rigid or flexible material, including, but not limited to, rubber, metal, polymeric materials, and combinations thereof.

Figure 7A:
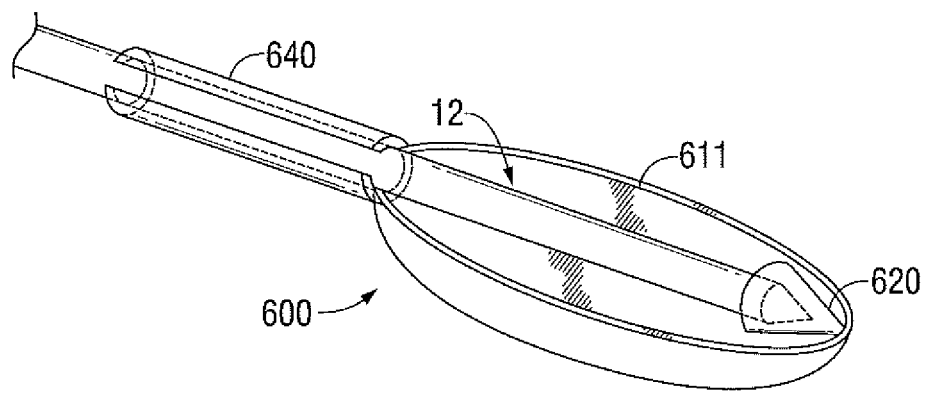
FIG. 7A is a partial, perspective view of the energy applicator of FIG. 2 shown operably associated with the directional reflector assembly of FIG. 6.
Figure 7B:
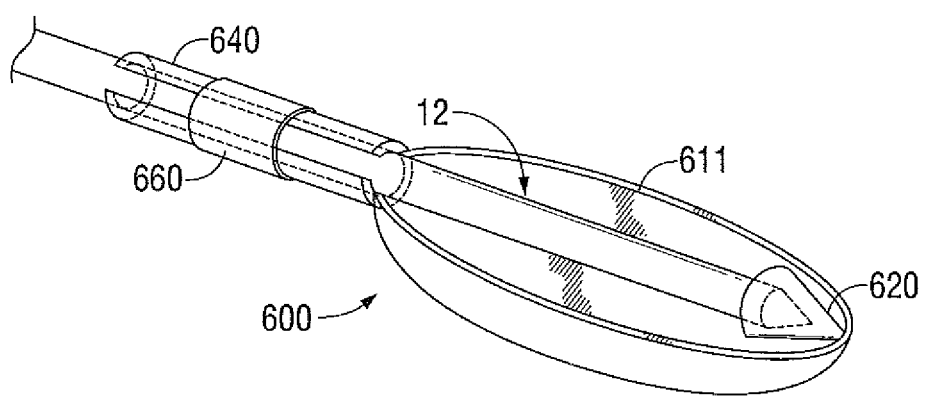
FIG. 7B is a partial, perspective view of the energy applicator and directional reflector assembly of FIG. 7A shown with a fastener element coupled to an attachment portion of the directional reflector assembly.

FIG. 7A shows the antenna assembly 12 of FIG. 2 operably associated with the directional reflector assembly 600 of FIG. 6. As shown in FIG. 7B, the second attachment portion 640 may be provided with a fastener element 660 generally adapted for releaseably closing the partial, cylindrically-shaped fastener element 660 around a proximal portion of the antenna assembly 12. Fastener element 660 may include any suitable fastener, such any suitable releasable fastener, coupleable to at least a portion of the outer surface of the second attachment portion 640. In embodiments, the fastener element 660 may include adhesive tape, wire, plastic tie cinch straps or other suitable tongue and groove type elongated flexible plastic fasteners, metal clips, plastic clips, fabric or plastic straps, VELCRO™ hook and loop brand type tapes, etc.

Figure 8:
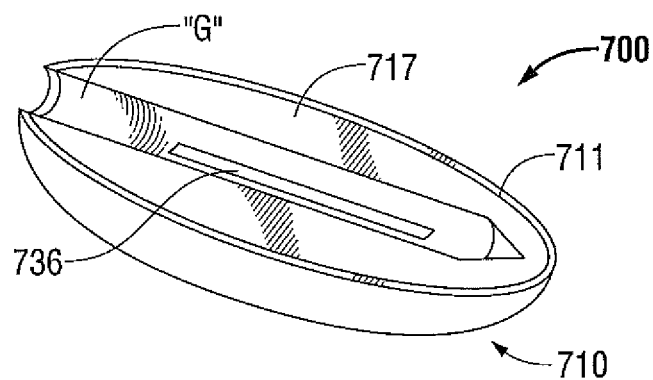
FIG. 8 is a perspective view of an embodiment of a directional reflector assembly in accordance with the present disclosure that includes an adhesive-receiving recess.

FIG. 8 shows a directional reflector assembly 700 according to an embodiment of the present disclosure that includes a shell assembly 710. Shell assembly 710 generally includes an outer portion 711 and an inner portion 717, and may include a recess in the form of a groove "G" defined in the planar surface "S" of the inner portion 717. Outer portion 711 is similar to the outer portion 511 shown in FIG. 4, and further description thereof is omitted in the interests of brevity.

Groove "G" is generally configured to receive a portion of an energy applicator therein. In embodiments, the groove "G" includes an adhesive-receiving recess 736 for receiving an adhesive material (e.g., "A" shown in FIG. 10) therein. Recess 736 may be any suitable shape, and may extend along the longitudinal axis of the groove "G". In embodiments, the length, depth and/or volume of the recess 736 may vary, e.g., depending on the material properties of the adhesive material "A" to be provided therein. In embodiments, the recess 736 may be single, elongated recess or a plurality of recesses.

Figure 9:
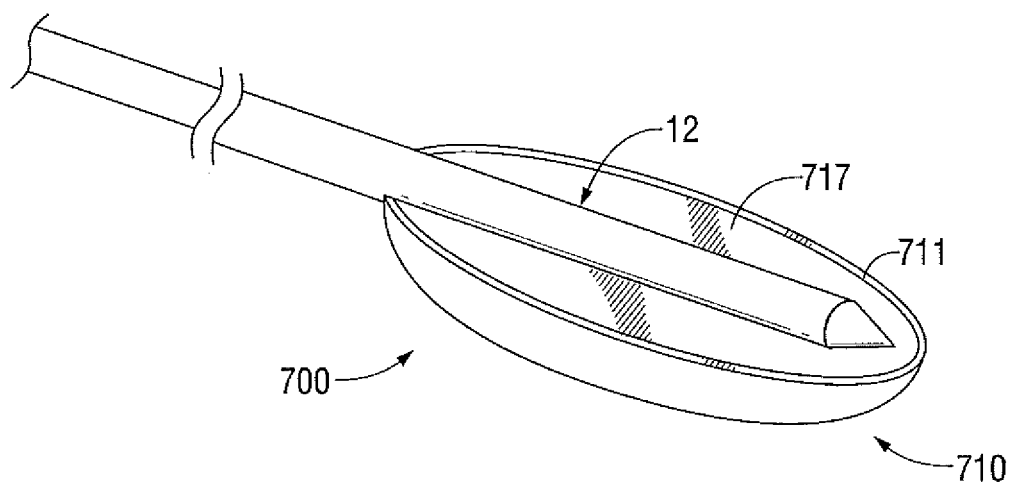
FIG. 9 is a partial, cross-sectional view of the energy applicator of FIG. 2 shown operably associated with the directional reflector assembly of FIG. 8.
Figure 10:
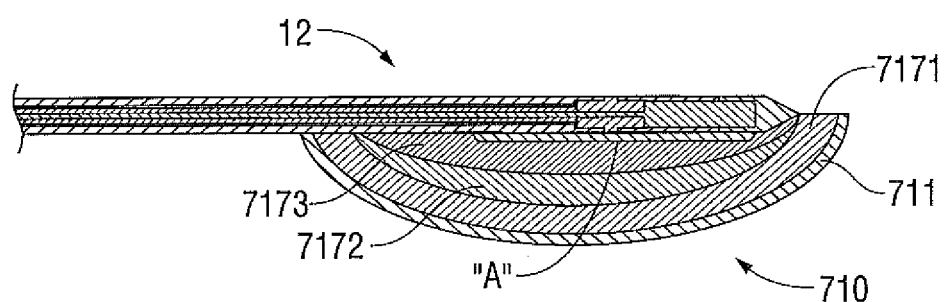
FIG. 10 is a cross-sectional view of the energy applicator of FIG. 2 shown operably associated with an embodiment of a directional reflector assembly in accordance with the present disclosure having a shell assembly including dielectric shells and an adhesive-receiving recess.

FIGS. 9 and 10 show the antenna assembly 12 of FIG. 2 operably associated with the directional reflector assembly 700 of FIG. 8. As shown in FIG. 10, the inner portion 717 of the shell assembly 710 may be formed of a first dielectric layer 7171, a second dielectric layer 7172 and a third dielectric layer 7173. Inner portion 717 may include any suitable number of dielectric layers in varied configurations. A variety of dielectric materials may suitably be used, including, but not limited to, polymers, ceramics, metal oxides and combinations thereof. In embodiments, the dielectric material used to form the third dielectric layer 7173 may have a relatively low dielectric constant k, such as k≈4. The thicknesses and dielectric constant k of the first, second and third dielectric layers, 7171, 7172 and 7173, respectively, may be optimized, e.g., based on the desired frequency and desired field pattern, to ablate an area of tissue to the desired depth.

Figure 11:
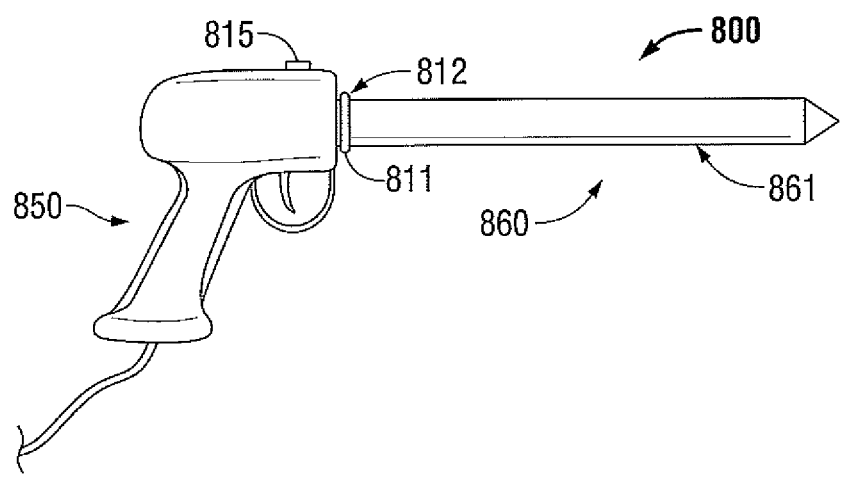
FIG. 11 is a perspective view of an embodiment of an energy applicator in accordance with the present disclosure that includes an ablation probe operably associated with a pistol-grip body and a male connector disposed at the proximal end of the probe.

FIG. 11 is a perspective view of an embodiment of an energy applicator 800 in accordance with the present disclosure that includes a pistol-grip body 850, a probe 860 extending distally therefrom., and a male connector 812 disposed at the proximal end of the ablation probe 860. Pistol-grip body 850 is operably associated with the male connector 812. In embodiments, the male connector 812 includes a retainer member 811 that is movable between at least an engagement position and a released position. In embodiments, the pistol-grip body 850 may include a user operable switch 815, e.g., a push button, operable to move the male connector 812 from an engagement position, in which the retainer member 811 is engaged with a female connector (e.g., 916 shown in FIGS. 12A and 14A-14C), to a released position, in which the retainer member 811 is disengaged from the female connector. The shape and size of the male connector 812 may be varied from the configuration depicted in FIG. 11.

Figure 12A:
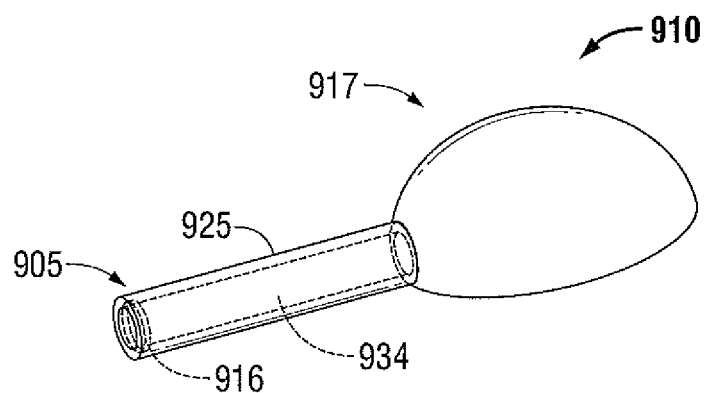
FIG. 12A is a perspective view of an embodiment of a directional reflector assembly in accordance with the present disclosure that includes a tubular portion having a female connector adapted for attachment to the male connector of the energy applicator of FIG. 11.
Figure 12B:
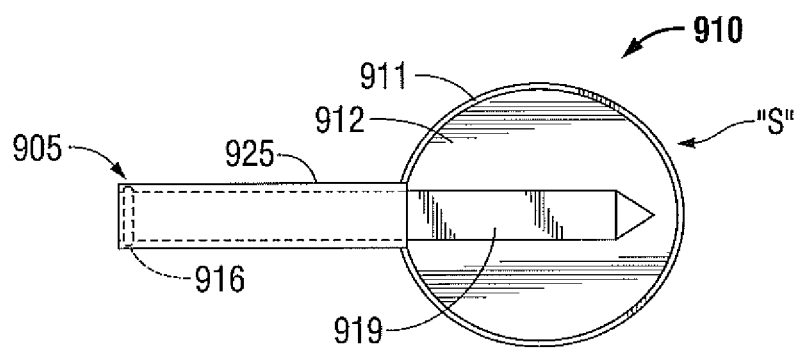
FIG. 12B is a bottom, perspective view of the directional reflector assembly of FIG. 12A.

FIGS. 12A and 12B show an embodiment of a directional reflector assembly 910 in accordance with the present disclosure that includes a shell assembly 917, a tubular portion 925 defining a lumen 934, and a female connector 916 associated with the proximal end 905 of the tubular portion 930. Female connector 916 is adapted for engagement with the male connector 812 of the energy applicator 800 of FIG. 11.

Shell assembly 917 generally includes an outer portion 911 and an inner portion 912, and may include a recess 919 defined in the planar surface "S" of the inner portion 912 generally configured to receive a distal end portion of an energy applicator therein. Shell assembly 917 is similar to the shell assembly 710 shown in FIG. 8, and further description thereof is omitted in the interests of brevity.

Figure 13A:
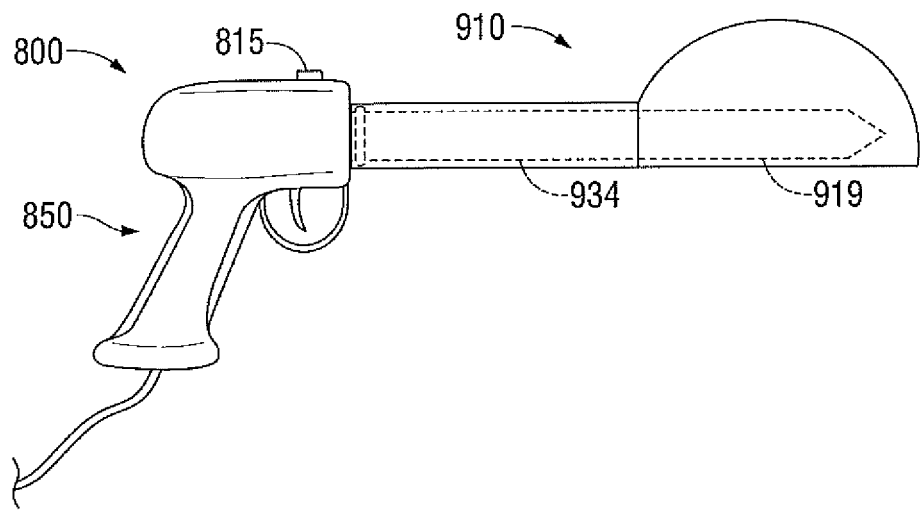
FIG. 13A is a perspective view of the energy applicator of FIG. 11 shown with the directional reflector assembly of FIG. 12A mounted on the probe shaft thereof.
Figure 13B:
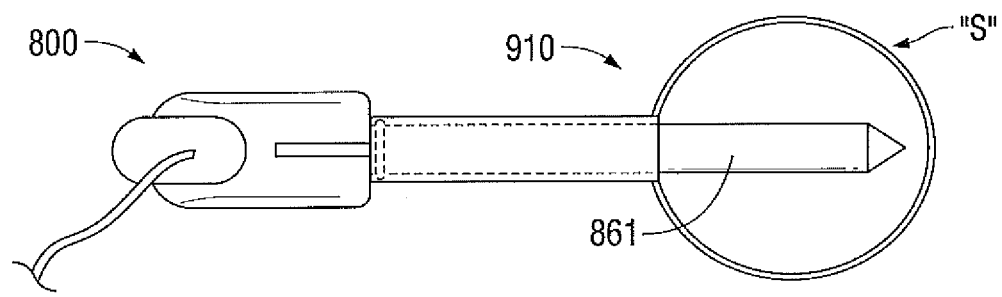
FIG. 13B is a bottom, perspective view of the energy applicator and the directional reflector assembly of FIG. 13A.

FIGS. 13A and 13B show the energy applicator of FIG. 11 with the directional reflector assembly of FIG. 12A mounted thereupon. As shown in FIGS. 13A and 13B, the lumen 934 is configured to receive the ablation probe 860, whereby the distal portion 861 of the ablation probe 860 extends across the planar surface "S" of the shell assembly 911.

Figure 14A:
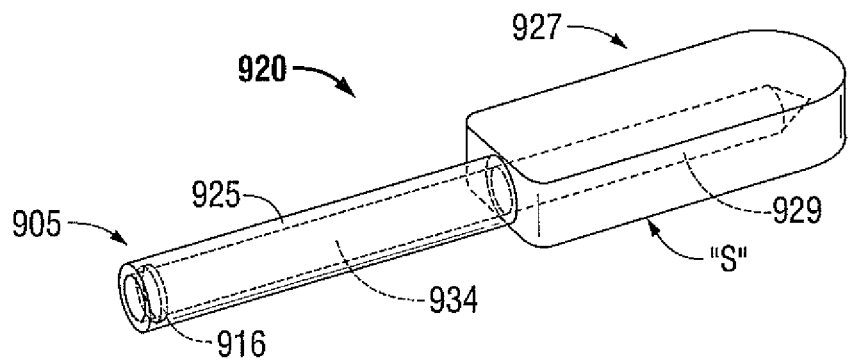
FIGS. 14A through 14C are perspective views of alternative embodiments of the directional reflector assembly of FIG. 12A.

FIG. 14A shows an embodiment of a directional reflector assembly 920 in accordance with the present disclosure that includes a shell assembly 927, a tubular portion 925 defining a lumen 934, and a female connector 916 associated with the proximal end 905 of the tubular portion 925. In embodiments, the shell assembly 927 has a paddle-like or thick butter knife shape, and may include a recess 929 defined in a planar surface "S" thereof. Shell assembly 927 is similar to the shell assembly 917 shown in FIG. 12A, except for its shape, and further description thereof is omitted in the interests of brevity.

Figure 14B:
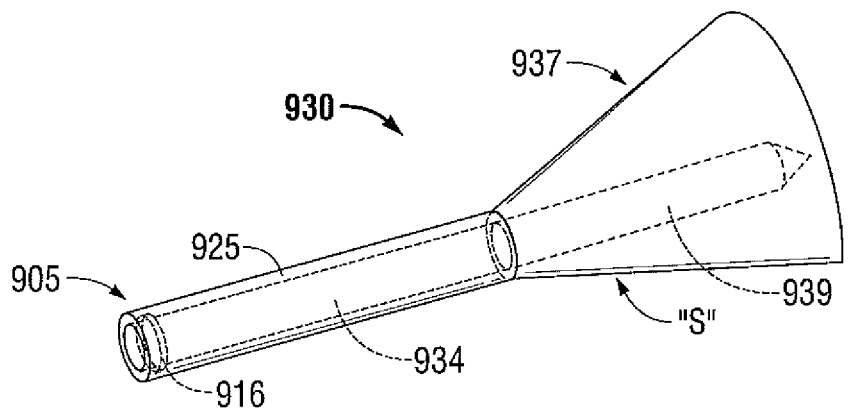

FIG. 14B shows an embodiment of a directional reflector assembly 930 in accordance with the present disclosure that includes a shell assembly 937, a tubular portion 925 defining a lumen 934, and a female connector 916 associated with the proximal end 905 of the tubular portion 925. In embodiments, the shell assembly 937 has a half-conical shape, and may include a recess 939 defined in a planar surface "S" thereof. Shell assembly 937 is similar to the shell assembly 917 shown in FIG. 12A, except for its shape, and further description thereof is omitted in the interests of brevity.

Figure 14C:
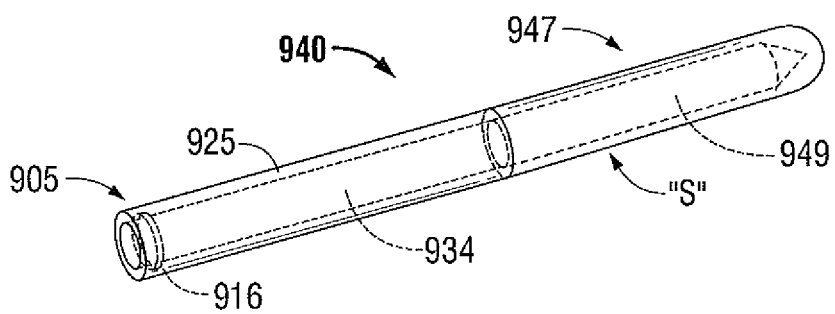

FIG. 14C shows an embodiment of a directional reflector assembly 940 in accordance with the present disclosure that includes a shell assembly 947, a tubular portion 925 defining a lumen 934, and a female connector 916 associated with the proximal end 905 of the tubular portion 925. In embodiments, the shell assembly 947 has a partial, cylindrical shape, and may include a recess 949 defined in a planar surface "S" thereof. Shell assembly 947 is similar to the shell assembly 917 shown in FIG. 12A, except for its shape, and further description thereof is omitted in the interests of brevity.

Figure 15:
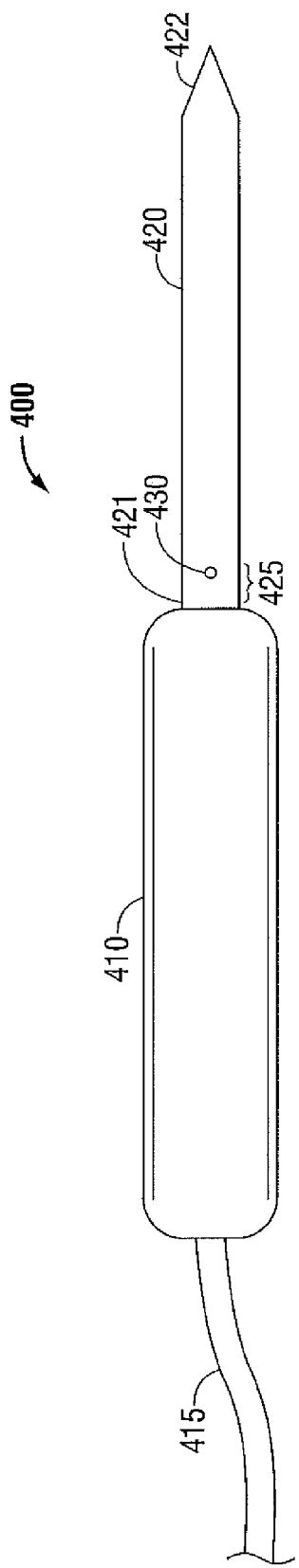
FIG. 15 is a side view of an ablation probe in accordance with the present disclosure having an alignment protrusion at a proximal end of a probe shaft thereof.
Figure 16:
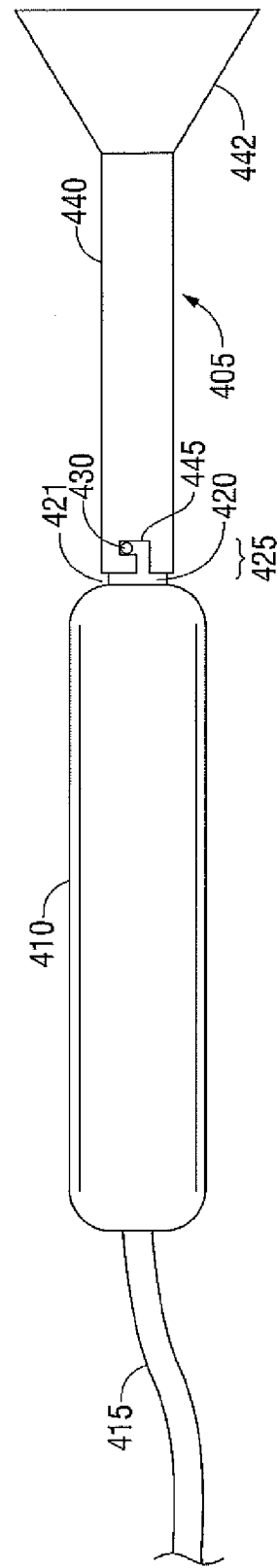
FIG. 16 is a side view of the ablation probe of FIG. 15 shown with a directional reflector assembly in accordance with the present disclosure mounted on the probe shaft.

In another embodiment as shown in FIGS. 15 and 16, microwave ablation probe 400 includes a handle 410 fixed at a distal end thereof to a shaft 420 having a tip 422. A cable 415 couples the probe 400 to a source of microwave ablation energy (not shown). A directional reflector assembly 405 includes a tubular shaft 440 and a conical aperture 442. Shaft 440 includes a coupling 425 having one or more slots 445 defined therein that are adapted to engage a protrusion 430 provided at a proximal end 421 of a probe shaft 420. The engagement of slot 445 with protrusion 430 may aid the positioning of outer tube 440 with probe shaft 420, and may additionally, or alternatively, provide positive retention of outer tube 440 to probe shaft 420 during use. Slot 445 and protrusion 430 may include a bayonet arrangement, as shown, and may additionally or alternative include any suitable coupling arrangement, such as without limitation, a threaded arrangement, an interference fit arrangement, or other coupling arrangement. Coupling 425 may additionally, or alternatively, be configured to provide coolant coupling (e.g., fluid or gas coupling) between the probe handle 410 and/or shaft 420, and a directional reflector assembly.

Figure 17:
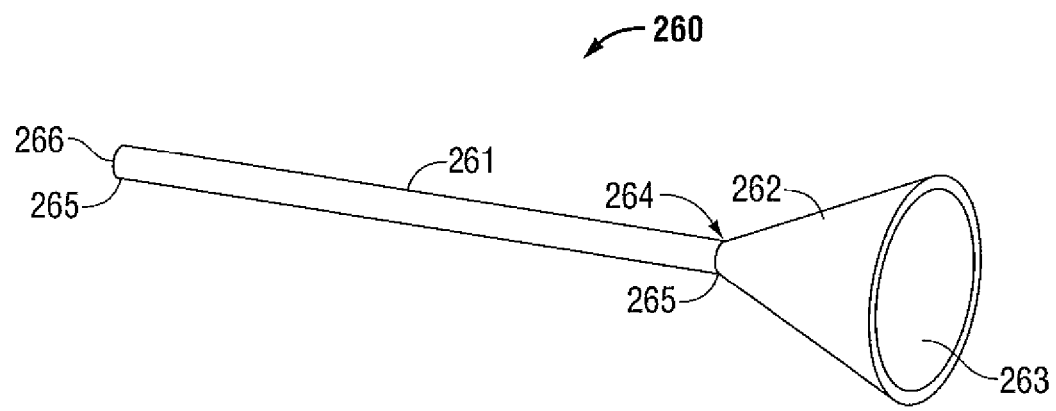
FIG. 17 is a perspective view of an embodiment of a directional reflector assembly in accordance with the present disclosure having an air-filled conical aperture.

FIG. 17 shows an embodiment of an air-filled directional reflector assembly 260 that includes an outer tube 261 having a distal end 264 and a proximal end 265 that is dimensioned to slideably engage a probe shaft (e.g., 420). Outer tube 261 may be formed from any suitable material, including without limitation metallic material (e.g., stainless steel) and/or dielectric material (e.g., epoxy fiber composite). A conical aperture 262 having a distal base opening 263 and a proximal apex opening 265 is joined at a proximal apex opening 265 thereof to a distal end 264 of shaft 261. For use, the directional reflector assembly 260 is positioned onto a recipient microwave ablation probe (not shown) by sliding a distal end of the probe into a proximal inner portion 266 of outer tube 261. A generally circular distal plate (not shown) having a circular opening disposed at a center thereof is fixed at a perimeter thereof to a distal open base of conical aperture 262.

Figure 18:
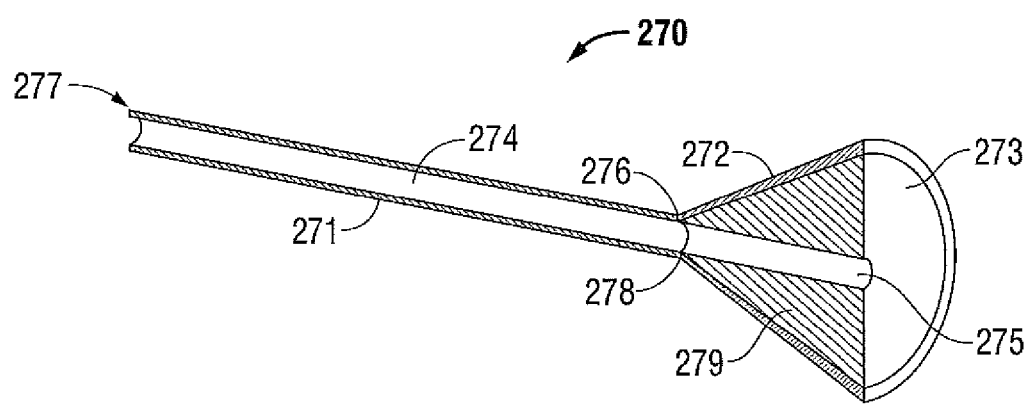
FIG. 18 is a perspective view of an embodiment of a directional reflector assembly in accordance with the present disclosure having a dielectric-filled conical aperture.

Turning to FIG. 18, an embodiment of a dielectric-filled directional reflector assembly 270 in accordance with the present disclosure is shown. Directional reflector assembly 270 includes an outer tube 271 having a distal end 276 and a proximal end 277 that is dimensioned to slideably engage a probe shaft as previously described herein. Outer tube 271 may be formed from any suitable material, as previously described herein. A conical reflector 272 having a distal base opening 273 and a proximal apex opening 278 is joined at the proximal apex opening 278 to a distal end 276 of shaft 271. Conical reflector 272 includes a dielectric core 279 disposed therein. An inner opening 274 defined within outer tube 271 is coupled to an inner opening 275 axially defined within dielectric core 279. An inner diameter of outer tube 271 (e.g., corresponding to the diameter of inner opening 274) is substantially equal to an inner diameter of inner opening 275 to form a substantially continuous opening 274 between tube 271 and a distal end of dielectric core 279 to accommodate the insertion of an ablation probe thereinto for use, as previously described herein.

In yet another embodiment according to the present disclosure shown in FIG, 14, a multilayer dielectric-filled directional reflector assembly 280 includes an outer tube 281 having an inner opening 284 defined longitudinally therein. A conical reflector 282 is joined at a proximal open apex end thereof to a distal end of outer tube 281. Conical reflector 282 includes at least a first dielectric core region 2831, that may be formed from a first dielectric material, and a second dielectric core region 2832, that may be formed from a second dielectric material. Additional dielectric core regions beyond a first and second are envisioned within the scope of the present disclosure, e.g., dielectric core region 2833. The dielectric core regions 2831 et seq. may have a flared conical shape and may be arranged such that the dielectric regions 2831 et seq. are coaxially disposed, as shown in FIG. 14. Additionally, or alternatively, the dielectric core regions may have other shapes and arrangement, including but not limited to, planar, interleaved, toroidal, radial, cylindrical, and polygonal extrusions.

An inner opening 284 defined within outer tube 281 is coupled to an inner opening 285 axially defined through the innermost multilayer dielectric core region, e.g., 2833. An inner diameter of outer tube 281 (e.g., corresponding to the diameter of inner opening 284) is substantially equal to an inner diameter of inner opening 285 to form a substantially continuous opening 284 between tube 281 and a distal end of multilayer dielectric core 2831 et seq. to accommodate the insertion of an ablation probe therein for use, as previously described herein.

Turning now to FIG. 20, a multilayer dielectric-filled directional reflector assembly 290 includes a tubular shaft 291 having an inner opening 294 defined longitudinally therein. A conical reflector 292 is joined at a proximal open apex end thereof to a distal end of tubular shaft 291. A generally circular distal plate 298 having a circular opening 299 disposed at a center thereof is fixed at a perimeter thereof to a distal open base of reflector 292. Circular distal plate 298 may be formed from material that is radiofrequency transparent at an operating frequency of a microwave ablation probe, which may be in a range of about 915 MHz to about 2.45 GHz. Circular distal plate 298 may additionally, or alternatively, be formed from a lubricious material, including without limitation, polytetrafluoroethylene (a.k.a. PTFE or Teflon®, manufactured by the E.I. du Pont de Nemours and Company of Wilmington, Del., United States).

Conical reflector 292 includes one or more dielectric core regions, e.g., 2931, 2932, 2933. The dielectric core regions 2931, 2932, 2933 et seq. may be formed from similar, or from dissimilar, dielectric materials. The dielectric core regions 2931 et seq. may have a flared conical shape and may be arranged coaxially, radially, or may have other shapes and arrangements, including but not limited to, planar, interleaved, toroidal, cylindrical, and polygonal extrusions. A longitudinal inner opening 294 defined within tubular shaft 291 is coupled to an inner opening 295 axially defined through an innermost dielectric core region, e.g., 2933. An inner diameter of tubular shaft 291 (e.g., corresponding to the diameter of inner opening 294) may be substantially equal to an inner diameter of inner opening 295 and to circular opening 299 to form a substantially continuous opening 294 between tube 291 and a distal surface of circular distal plate 298 to accommodate the insertion of an ablation probe therein for use, as previously described herein.

FIG. 21 illustrates yet another embodiment wherein a directional reflector assembly 300 includes a dual-wall cooled shaft 301. The cooled shaft 301 includes an inner tube 309 coaxially disposed within an outer tube 308 having a cooling region 307 disposed therebetween. Cooling region 307 may include thermally-conductive material (e.g., copper) and/or heat pipe that is adapted to transfer thermal energy from the shaft 301 and/or a conical reflector 302 by conduction or convection. Cooling region 307 may additionally, or alternatively, include fluid coolant. Examples of coolant include, but are not limited to, liquids such as deionized water, or saline. Gaseous coolant (e.g., air or biocompatible refrigerant) may also be utilized. Cooling region may extend distally into conical reflector 302 along a channel 305 defined between an outer surface of inner tube 309 and an inner surface of an innermost dielectric core region, e.g., 3033. A generally circular distal plate 306 having a circular opening 3061 disposed at a center thereof is fixed at a perimeter thereof to a distal open base of reflector 302. Circular distal plate 306 may be formed from material that is radiofrequency transparent and/or lubricious as previously described herein. Conical reflector 302 may include one or more dielectric core regions, e.g., 3031, 3032, 3033 et seq. as previously described, which may be formed from similar, or from dissimilar, dielectric materials. Inner tube 309 extends distally into conical reflector 302 to form a continuous opening 304 defined axially within the directional reflector assembly 300, e.g., from a proximal end of shaft 301 to a distal surface of cover 306 to accommodate the insertion of an ablation probe therein for use, as previously described.

With reference now to FIG. 22, a fluid-cooled directional reflector assembly 310 includes a dual-wall cooled shaft 311 having an outer tube 318, an inner tube 317 coaxially disposed therein and defining an opening 314, and a fluid path 319 defined therebetween. A conical aperture 312 is joined to a distal end of the outer tube 318. Conical aperture 312 includes a dielectric 313 disposed therein. A cooling chamber 315 having a proximal end in fluid communication with a distal end of fluid path 319 is defined within the dielectric 313. A generally circular distal plate 316 having a circular opening 3162 defined at a center thereof is fixed at least at a perimeter 3161 thereof to a distal rim 3121 of an open base of reflector 312 and adapted to form a sealed distal end of cooling chamber 315. Circular distal plate 316 may additionally, or alternatively, be joined at the center thereof to an outer surface and/or distal end of inner tube 317. During use, coolant may circulate through fluid path 319 and or cooling chamber 315, which may help control the temperature of the attachment 310, and may provide dielectric loading within the aperture 312. Circular distal plate 316 may be formed from fluid-impermeable material that is radiofrequency transparent and/or lubricious, such as without limitation, PTFE.

As shown in FIG. 23, a fluid-cooled directional reflector assembly 320 may include a conical aperture 322 having a cooling chamber 325 defined therein by the interior volume of the aperture 322 and a circular distal plate 326. Circular distal plate 326 is fixed at an outer perimeter 3261 thereof to a distal rim 3221 of conical aperture 322. Circular distal plate 326 may additionally, or alternatively, be fixed at a perimeter of an opening 3262 define therein to a distal outer surface of inner tube 327.

FIG. 24 depicts a fluid-cooled directional reflector assembly 330 having a single-walled tubular shaft 331 defining an opening 334 therein and joined at a distal end thereof to a proximal open apex 333 of conical aperture 332. A circular distal plate 336 fixed at an outer perimeter 338 thereof to a distal rim 335 of conical aperture 322 to define a coolant chamber 339 within the conical aperture 322. Circular distal plate 336 additionally, or alternatively, includes an opening 337 defined therein that is joined at a perimeter thereof to a distal outer surface of tubular shaft 331. Coolant chamber 339 contains coolant 3391, for example, and without limitation, saline, sterile water, and/or deionized water, which may enhance cooling and/or improved dielectric loading during use.

A directional reflector assembly in accordance with the present disclosure may include one or more baluns, which may improve the radiation and/or ablation pattern provided during use. More particularly, and with reference now to FIG. 25, a directional reflector assembly 340 includes a tubular shaft 341 defining an opening 344 therein and joined at a distal end thereof to a proximal open apex 343 of a conical aperture 342. A circular distal plate 346 is disposed at a distal open end of the conical aperture 342 in a manner previously described herein. A dielectric core 347 is disposed within the conical aperture 342. A balun 345 is concentrically disposed around at least a part of tubular shaft 341, e.g., along a distal portion of the shaft 341 and substantially adjacent to the proximal open apex 343 of the conical aperture 342. Balun 345 may include a ring-like balun short 349 concentrically disposed around the shaft 341 at a proximal end of the balun 345 and electrically coupled thereto. A balun dielectric layer 348 may additionally, or alternatively, be concentrically disposed between the balun 345 and the shaft 341.

In yet another embodiment shown in FIG. 26, an air-filled directional reflector assembly 350 includes a tubular shaft 351 defining an opening 354 therein and joined at a distal end thereof to a proximal open apex 357 of a conical aperture 352. A first balun 355 is concentrically disposed around at least a part of tubular shaft 351, e.g., along a distal portion of the shaft 351 and substantially adjacent to the proximal open apex 357 of the conical aperture 352. First balun 355 may include a ring-like balun short 359 concentrically disposed around the shaft 351 at a proximal end of the balun 355 and electrically coupled thereto. A first balun dielectric layer 358 may additionally, or alternatively, be concentrically disposed between the balun 355 and the shaft 351. Conical aperture 352 includes a second balun dielectric layer 353 disposed between an inner surface of conical aperture 352 and a second balun 356. First balun 355 and second balun 356 may be electrically coupled.

Figure 27:
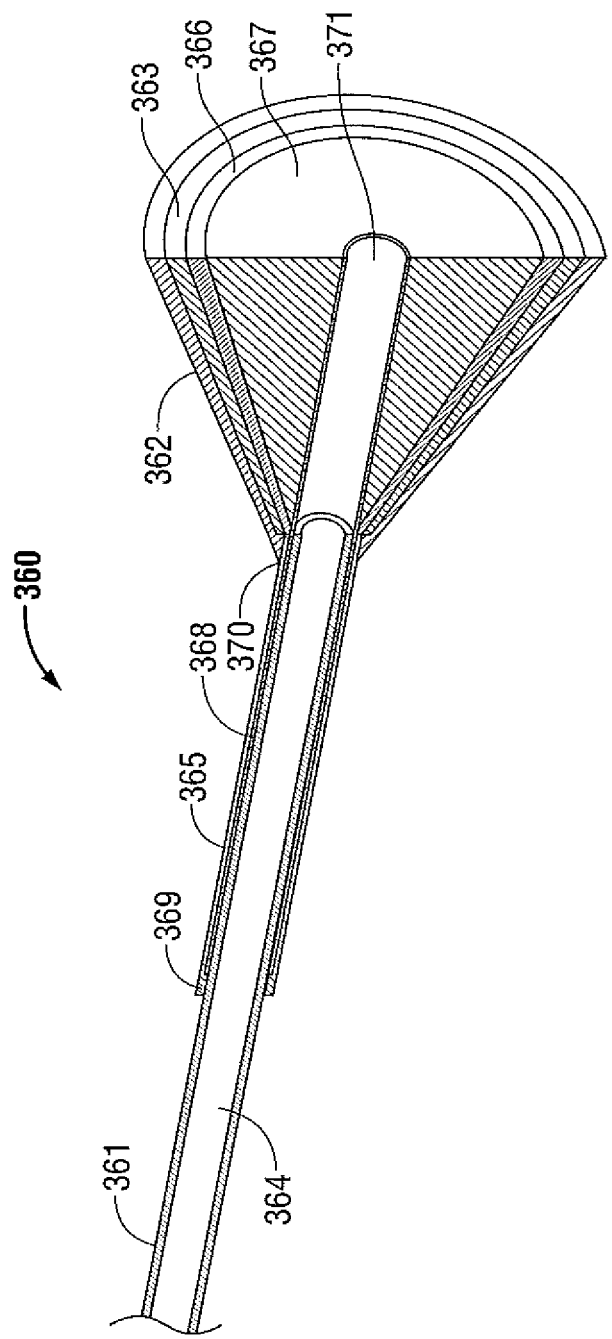
FIG. 27 is a perspective view of an embodiment of a directional reflector assembly in accordance with the present disclosure that includes a dielectric-filled conical aperture and a balun positioned over the shaft and within the cone.

FIG. 27 illustrates still another embodiment in accordance with the present disclosure that may include a shaft balun, a cone balun, and/or a dielectric core. In more detail, a dielectric core directional reflector assembly 360 includes a tubular shaft 361 that is joined at a distal end thereof to a proximal open apex 370 of a conical aperture 362. A first balun 365 is concentrically disposed around at least a part of tubular shaft 361, e.g., along a distal portion of the shaft 361 and substantially adjacent to the proximal open apex 370 of conical aperture 362. First balun 365 may include a ring-like balun short 369 concentrically disposed around the shaft 361 at a proximal end of the balun 365 and electrically coupled thereto. A first balun dielectric layer 368 may additionally, or alternatively, be concentrically disposed between the balun 365 and the shaft 361. Conical aperture 362 includes a second balun dielectric layer 363 disposed between an inner surface of conical aperture 362 and a second balun 366. First balun 365 and second balun 366 may be electrically coupled. Conical reflector 362 includes a dielectric core 367 disposed therein, e.g., within an inner surface of second balun 366. An inner opening 364 defined within outer shaft 361 is coupled to an inner opening 371 axially defined within dielectric core 367. An inner diameter of outer shaft 361 (e.g., the diameter of inner opening 364) is substantially equal to an inner diameter of inner opening 371 to form a substantially continuous opening 364 between a proximal end of outer shaft 361 and a distal end of dielectric core 361 to accommodate the insertion of an ablation probe thereinto for use, as previously described herein.

The above-described directional reflector assemblies and electrosurgical devices for treating tissue and methods of directing electromagnetic radiation to a target volume of tissue may be used to provide directional microwave ablation, wherein the heating zone may be focused to one side of the electrosurgical device, thereby allowing clinicians to target small and/or hard tumors without having to penetrate the tumor directly or effect more healthy tissue than necessary. The presently disclosed electrosurgical devices and directional reflector assemblies may allow clinicians to avoid ablating critical structures, such as large vessels, healthy organs or vital membrane barriers, by placing the electrosurgical device between the tumor and critical structure and directing the electromagnetic radiation toward the tumor and away from the sensitive structure.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A directional reflector assembly, comprising:
a hollow tubular shaft having a proximal end and a distal end, the hollow tubular shaft defining an inner opening therein extending longitudinally from the proximal end to the distal end, the inner opening configured to slideably engage an electrosurgical ablation probe;
a conical aperture having a proximal open apex and a distal open base, an interior volume of the conical aperture defined therein between the proximal open apex and the distal open base, wherein the entire circumference of the proximal open apex of the conical aperture is joined to the distal end of the hollow tubular shaft; and
a dielectric core disposed within the interior volume of the conical aperture, the dielectric core defining a lumen extending therethrough from the proximal open apex to the distal open base, the lumen communicatively-coupled with the inner opening of the hollow tubular shaft and axially aligned therewith, wherein the lumen is configured to receive a portion of an electrosurgical ablation probe translatable therein from the proximal open apex to the distal open base, and wherein the interior volume of the conical aperture is filled by the dielectric core except for the lumen extending therethrough from the proximal open apex to the distal open base.

2. The directional reflector assembly in accordance with claim 1, wherein the hollow tubular shaft includes at least one slot defined near a proximal end thereof that is adapted to operably engage a corresponding protrusion disposed on the electrosurgical ablation probe.

3. A directional reflector assembly, comprising:
a hollow tubular shaft having a proximal end and a distal end, the hollow tubular shaft defining an inner opening therein extending longitudinally from the proximal end to the distal end, the inner opening configured to slideably engage an electrosurgical ablation probe;
a conical reflector configured to be operably coupleable to the distal end of the hollow tubular shaft, the conical reflector including a proximal open apex, a distal open base, and an interior volume defined therein between the proximal open apex and the distal open base, wherein the entire circumference of the proximal open apex of the conical reflector is joined to the distal end of the hollow tubular shaft; and
a dielectric core disposed within the interior volume and defining a lumen extending therethrough from the proximal open apex to the distal open base, the lumen communicatively-coupled with the inner opening of the hollow tubular shaft and axially aligned therewith, wherein the lumen is configured to receive a portion of an electrosurgical ablation probe translatable therein from the proximal open apex to the distal open base, wherein the interior volume of the conical reflector is filled by the dielectric core except for the lumen extending therethrough from the proximal open apex to the distal open base.

4. A directional reflector assembly, comprising:
a hollow tubular shaft having a proximal end and a distal end, the hollow tubular shaft defining an inner opening therein extending longitudinally from the proximal end to the distal end, the inner opening configured to slideably engage an electrosurgical ablation probe;
a conical reflector configured to be operably coupleable to the distal end of the hollow tubular shaft, the conical reflector including a proximal open apex, a distal open base, and an interior volume defined therein between the proximal open apex and the distal open base, the proximal open apex joined to the distal end of the hollow tubular shaft; and a dielectric core disposed within the interior volume, wherein the interior volume is filled by the dielectric core except for a lumen extending therethrough from the proximal open apex to the distal open base, the lumen communicatively-coupled with the inner opening of the hollow tubular shaft and axially aligned therewith, wherein the lumen is configured to receive a portion of an electrosurgical ablation probe translatable therein from the proximal open apex to the distal open base.

* * * * *